United States Patent [19]

Tahir et al.

[11] Patent Number: 5,319,115

[45] Date of Patent: Jun. 7, 1994

[54] METHOD FOR MAKING 3α-HYDROXY, 3β-SUBSTITUTED-PREGNANES

[75] Inventors: Hasan Tahir, Pasadena; Michael Bolger, Los Alamitos; Richard Buswell, Santa Rosa, all of Calif.; Richard Gabriel, Woburn, Mass.; Jay Stearns, Santa Rosa, Calif.

[73] Assignee: Cocensys Inc., Irvine, Calif.

[21] Appl. No.: 846,193

[22] Filed: Mar. 4, 1992

Related U.S. Application Data

[63] Continuation-in-part of Ser. No. 745,216, Aug. 13, 1991, Pat. No. 5,232,917, which is a continuation-in-part of Ser. No. 521,724, May 10, 1990, Pat. No. 5,120,723, which is a continuation-in-part of Ser. No. 379,047, Jul. 13, 1989, abandoned, which is a continuation-in-part of Ser. No. 89,362, Aug. 25, 1987, abandoned.

[51] Int. Cl.$^5$ .............. C07J 21/00; C07J 43/00; C07J 41/00
[52] U.S. Cl. .............. 552/609; 540/6; 540/28; 540/120; 540/95; 540/96; 540/99; 540/108; 540/109; 540/114; 552/508; 552/539; 552/544; 552/546; 552/552
[58] Field of Search .......... 540/95, 96, 99, 108, 540/109, 114, 120, 6, 28; 552/508, 544, 546, 552, 609, 539

[56] References Cited

U.S. PATENT DOCUMENTS

| | | | |
|---|---|---|---|
| 3,466,276 | 9/1969 | Campbell et al. | 540/95 |
| 3,600,412 | 8/1971 | Nelson | 540/95 |
| 3,697,509 | 10/1972 | Colton et al. | 540/109 |
| 3,900,467 | 8/1975 | Irmscher et al. | 540/95 |
| 4,501,695 | 2/1985 | Van Rheenen | 540/95 |
| 4,519,946 | 5/1985 | Teutsch et al. | 540/99 |
| 5,034,548 | 7/1991 | Gaylor et al. | 540/120 |
| 5,081,113 | 1/1992 | Claussner et al. | 540/109 |
| 5,120,723 | 6/1992 | Gee et al. | 540/99 |

OTHER PUBLICATIONS

ElSayed S. Arafat et al., Am. J. Obstet Gynecol. 1988 p. 1203.
Conney et al., The Journal of Pharm. and Experimental Therapeutics 1966, p. 310.
Gyermek, Pregnanolone: Steroid Hypnotic Agent p. 1058 (1967).
Gyermek et al. Int. J. Neuropharmacol. 1967, 6, 191–198.
Mendelson et al., Psychopharmacology (1987) 93:226–229.
Raisinghani et al., Acta Endocrinologica 57(1968) 395–404.

*Primary Examiner*—Cecilia Tsang
*Attorney, Agent, or Firm*—Lyon & Lyon

[57] ABSTRACT

This invention provides a simplified method for converting pregnan-3,20-dione compounds to 3α-hydroxy,3β-substituted-pregnanes. By selective use of reagents the unprotected dione is converted chemoselectively and diastereoselectively into a 3(R)-pregnan-3-spiro-2'oxirane-20-one intermediate. This intermediate can then be converted regioselectively by a second set of reactions to the 3α-hydroxy,3β-substituted-20-one form, which can be further modified at the 20-keto position.

Through this method, each ketone group is independently treated. By modifying the ketones one at a time, one can obtain the desired stereo-specificity at each site.

16 Claims, 1 Drawing Sheet

METHOD FOR MAKING 3α-HYDROXY, 3β-SUBSTITUTED-PREGNANES

This application is a continuation-in-part of copending application Ser. No. 745,216 filed Aug. 13, 1991, which is in turn a continuation-in-part of copending application Ser. No. 521,724, filed May 10, 1990 now U.S. Pat. No. 5,120,723 which is in turn a continuation-in-part of copending application Ser. No. 379,047, filed Jul. 13, 1989 now abandoned, which in turn is a continuation-in-part of application Ser. No. 089,362 filed Aug. 25, 1987, now abandoned. These applications and their claims and figures are incorporated herein by reference.

BACKGROUND OF THE INVENTION

The present invention is directed to a method for making compositions and compounds useful for modulating animal brain excitability via the gamma-aminobutyric acid (GABA) receptor-chloride ionophore complex (GR complex).

A variety of steroid derivatives, such as 3α-hydroxy,3β-methyl-5α-pregnan-20-one, have been shown to be effective in stimulating the GR complex, with a variety of physiological effects. See U.S. Ser. No. 07/745,216, 07/521,724, and 07/379,047, incorporated herein by reference. The standard procedure for making this compound and other 3α-hydroxy,3β-substituted-pregnanes includes a step wherein compounds with two keto groups have one group protected prior to reaction at the other keto group to produce a 3β-substituted pregnane. During this process, one method of protecting the 20-keto group is to change it to an ethylene ketal group. See U.S. Pat. No. 3,953,429. The drawbacks of this method include the requirement for the use of two steps--protection before reaction at the 3-keto position and deprotection after reaction--with their accompanying loss in material.

We have discovered a novel method for production of 3α-hydroxy, 3β-substituted-pregnanes which does not require protection of the 20-one group. By this method, each ketone group is treated independently. A variety of groups can be substituted into the 3β position. The ketone at the 20 position can also be modified in an independent manner.

SUMMARY OF THE INVENTION

This invention provides a simplified method for converting pregnan-3,20-dione compounds to 3α-hydroxy,3β-substituted-pregnanes. By selective use of reagents the unprotected dione is converted chemoselectively and diastereoselectively into a 3(R)-pregnan-3-spiro-2'oxirane-20-one intermediate. This intermediate can then be converted regioselectively by a second set of reactions to the 3α-hydroxy, 3β-substituted-20-one form, which can be further modified at the 20-keto position.

Through this method, each ketone group is independently treated. By modifying the ketones one at a time, one can obtain the desired stereo-specificity at each site.

BRIEF DESCRIPTION OF THE DRAWINGS

The present invention may be better understood and its advantages appreciated by those skilled in the art by referring to the accompanying drawing wherein.

DETAILED DESCRIPTION

Figure 1:
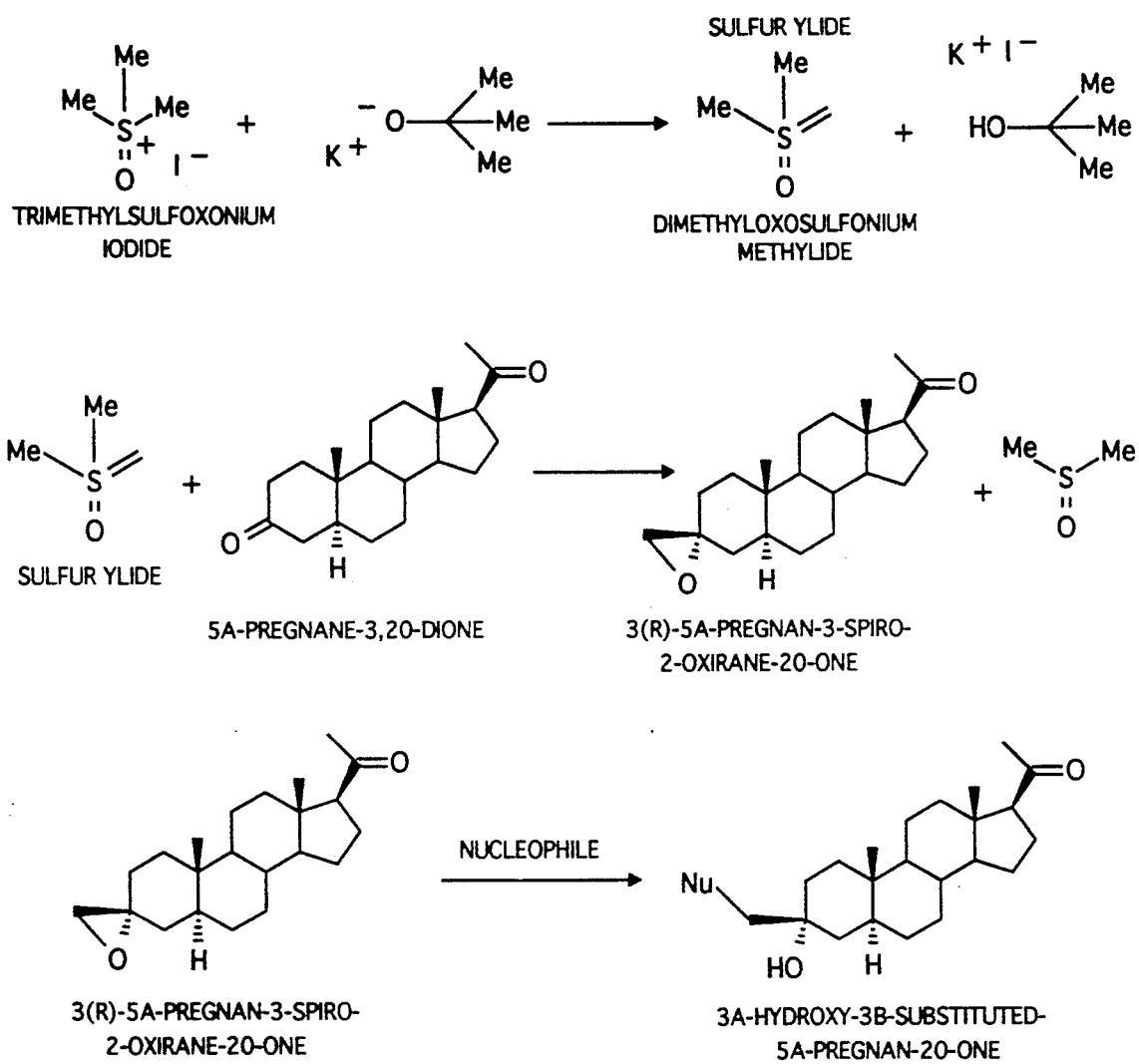
FIG. 1 is a synthetic reaction diagram for the preparation of 3α-hydroxy-3β-substituted-5-pregnan-20-one from 5-α-pregnan-3,20-dione by sequential reaction with dimethyloxosulfonium methylide and then a nucleophole.

The starting materials for this reaction are pregnan-3,20-diones. The first step converts the ketone at the 3 position into an oxirane.

For this reaction, Corey's reagent and base are mixed in a suitable aprotic polar solvent to form any slide. Corey, et al., "Dimethylsulfoxonium Methylide and Dimethylsulfonium Methylide Formation and Application to Organic Synthesis," J. Amer. Chem. Soc. 87:1354–1364, 1965. The ylide is mixed with the pregnan-3,20-dione which has been suspended or dissolved in the solvent of choice. Sufficient reagent is provided to produce an amount of ylide that will give complete reaction of the ketone. The amount of base used to produce the ylide should be chosen so as to leave no unreacted base after formation of the ylide. The reaction is performed in a dry atmosphere, such as under nitrogen or argon gas, with dry solvents (in the absence of water). The time and temperature of ylide formation and subsequent reaction with ketone are determined by monitoring loss of ketone starting material or formation of oxirane product using a suitable analytical technique such as TLC or HPLC.

The reagent can be any Corey's reagent which reacts chemoselectively so as to selectively convert only the 3-keto group to an oxirane. The reagent is also chosen for the ability to diastereoselectively convert the 3-keto group to the desired oxirane, in this case a 3(R)-pregnan-3-spiro-2'oxirane-20-one. This reagent is preferably trimethyl sulfoxonium iodide, but any equivalent reagent which will react with the appropriate selectivity will do.

The reagent is dissolved in an appropriate aprotic, polar solvent, such as polyethers, amides, phosphoric amides, sulfoxides, sulfolanes. Specific examples are dimethylsulfoxide (DMSO), tetrahydrofuran (THF), hexamethylphosphoric triamide (HMPT), sulfolane, N-methyl-pyrolidone, dioxane, dimethoxyethane (DME), and dimethylformamide (DMF).

The base is chosen so that its basicity is sufficiently high to remove a proton from Corey's reagent in order to form the ylide. Examples of appropriate bases are NaH, potassium t-butoxide, and NaNH$_2$.

The oxirane group is then regioselectively opened to form the 3α-hydroxy,3β-substituted compounds. The reaction is performed in a dry atmosphere, such as under nitrogen or argon gas, with dry solvents (in the absence of water). Time of reaction and temperature are sufficient to insure complete reaction, as monitored by analytical techniques such as HPLC or TLC.

Opening of the oxirane is performed by reaction with an appropriate nucleophile which will open the oxirane without affecting the remaining 20-keto group. Preferred nucleophiles include alkoxides, thioalkoxides, azides, cyanide, isocyanide, amines, and halide anions such as iodide. Bonini et al., "A Facile Chemo and Regioselective Reductive Opening of 1,2 Epoxides Via Free Radical Reaction," Tetrahedron Letters, 29:819–822, 1988.

The oxirane can optionally be opened and subsequently converted to the 3β-methyl compound. Hydrogenolysis can be performed with hydrogen gas and a suitable catalyst. Examples of such a catalyst are transition metals such as palladium and platinum, dissolved in the appropriate solvent. The catalysts can be provided complexed to activated carbon. Other reagents for the reduction of the C-X bond (where X stands for halide) include trialkyl tin hydrides.

Optionally, a weak base such as sodium acetate can be added to the reaction after the oxirane ring is opened in order to remove acid formed as a byproduct during hydrogenolysis.

A nucleophile can also add to the oxirane at the 3' position. For example, a 3β-ethyl compound can be produced using dimethyl lithium cuprate; a 3β-bromomethyl compound can be produced using sodium bromide; a 3β-azidomethyl compound can be produced using sodium azide or trimethylsilyl azide; a 3β-propyl compound can be produced using diethyl lithium cuprate. The nucleophile is selected for its ability to regioselectively provide the desired group upon opening of the ring.

Any solvent capable of dissolving a sufficient quantity of the reagents to promote the reaction is appropriate. Examples of appropriate solvents are 1,2-dimethoxyethane, and a combination of THF and methanol. Aprotic polar solvents enhance the reaction by stabilizing the transition state and are therefore preferred.

The following examples of this procedure are provided for illustrative purposes. One skilled in the art will recognize that other reagents, solvents and bases can be substituted. Additionally one skilled in the art will recognize that similar starting compounds can also be used.

EXAMPLE 1

(3R)-5α-pregnan-3-spiro-2'oxirane-20-one

To a stirred solution of trimethyl sulfoxonium iodide (5.290 g, 24.04 mmol) in DMSO (75 mL) at room temperature was added NaH (97%; 488 mg, 19.72 mmol) in one portion. The resulting mixture that became a clear solution after ~10 min was stirred at room temperature under a nitrogen atmosphere for 1 h. Then a suspension of 5α-pregnan-3,20-dione (1.538 g, 4.860 mmol) in DMSO (40 mL + 10 mL for the rinse) was added dropwise through a pressure-equalizing funnel. The mixture so obtained, which was not completely clear, was stirred at room temperature under a nitrogen atmosphere for a total of 2.5 h although TLC (3:1 hexane/EtOAC) after 1.5 h showed complete disappearance of the starting material. The mixture was then poured into ice/water and extracted with ether (x3). The combined organic phase was washed with water (x3) and brine, dried (MgSO$_4$), filtered, and evaporated under reduced pressure to give a solid. Finally, recrystallization from hot 1:1 methanol/acetone (~50 mL) gave the epoxide (1.176 g, 73%) as white crystals.

EXAMPLE 2

(3R)-5α-pregnan-3-spiro-2'oxirane-20-one

A dry 3-neck flask with argon atmosphere, fitted with a mechanical stirrer, was charged with 400 mL of dry tetrahydrofuran and 34.0 g (0.29 moles) of potassium t-butoxide. After stirring the solution for thirty minutes, 63.1 g (0.29 moles) of trimethyl sulfoxonium iodide was added and the suspension stirred at ambient temperature for 2.0 hours, resulting in a heterogenous mixture. In a separate flask cooled 15°-20 C was slurried 80.0 g (0.26 moles) of powdered 5α-pregnane-3,20-dione in 400 mL dry tetrahydrofuran. The ylid was then slowly added to the steroid slurry, which was stirred for 1.5 hours at ambient temperature. The reaction was followed by TLC. The solids, potassium iodide and unreacted trimethylsulfoxonium iodide, were then removed by filtration (fast paper) or decantation. The solids were washed with ethyl acetate and the organic layers combined, or washed with dichloromethane and the washes added to the dichloromethane extract below. The reaction solvent was removed on an evaporator to afford a solid material. The solids were then washed with phosphate buffer (pH 7.5) (1.2 g (8.7 mmol) KH$_2$PO$_4$ and 3.55 g (30.4 mmol) Na$_2$HPO$_4$ (anh) in 1 L water), then taken up in 1.5 L dichloromethane, and 500 mL water. Both layers were separated and saved. The organic layer was washed successively with phosphate buffer (2X, pH 7.5), and 300 mL saturated brine. If an emulsion formed, more dichloromethane (or methanol) was added to help break the emulsion. The combined aqueous washes were back-extracted with dichloromethane (2X 200 mL). The combined organic fractions were dried over anhydrous sodium sulfate and the solvent removed on an evaporator to afford an off-white solid that could be recrystallized from methanol or ethanol.

EXAMPLE 3

3α-hydroxy-3β-methyl-5α-pregnan-20-one

To a solution (light yellow) of the (3R)-5α-pregnan-3-spiro-2'-oxirane-20-one (101 mg, 0.305 mmol) and NaI (115 mg, 0.767 mmol) in anhydrous 1,2-dimethoxyethane (DME) (5mL) at room temperature was added η-Bu$_3$SnH (0.22 mL, 0.238 g, 0.818 mmol). The reaction solution became colorless. Azobisisobutylnitrile (AIBN) (10 mg, 0.061 mmol) was then added. The resulting solution was refluxed under a nitrogen atmosphere for 21 h. at which point TLC (3:1 hexane/acetone) indicated completion of the reaction. The reaction was quenched with methanol; the mixture was stirred at room temperature for a while. The solvent was removed in vacuo to give an oil which did not dissolve in ether. Addition of CH$_2$Cl$_2$ gave a solution which was washed with water, 1N HCl, and saturated NaHCO$_3$. The organic layer was dried (MgSO$_4$), filtered, and concentrated under reduced pressure to a white solid. Purification by gradient flash chromatography (hexane, 7:1 hexane/acetone, 5:1 hexane/acetone) furnished the titled compound (93mg, 92%).

EXAMPLE 4

Preparation of
3α-hydroxy-3β-methyl-5α-pregnan-20-one

A suitable sized flask was charged with 100 g (0.316 mole) of 5α-pregnan-3-spiro-2'-oxirane-20-one, 70 g (0.47 mol) sodium iodide, 40 ml (0.7 mol) glacial acetic acid, and 1.5 L of 50:50 tetrahydrofuran/methanol. The solution was stirred at 65° C. for 1-2 hr. The reaction was followed by TLC (25% EtOAc/Hexanes, n-phase silica; develop iodine; approx. Rf epoxide 0.75, iodide 0.65). After complete consumption of starting epoxide, 70 g (0.85 mol) of anhydrous sodium acetate was added. After flushing the reaction flask with nitrogen 20 g (20% by wt) of 5% Pd/Carbon was carefully added. The reaction flask was flushed with nitrogen (2x) and hydrogen (2x), then charged with hydrogen (45 psia). The reaction was shaken for 16 hours at ambient temperature, then checked for completeness by TLC (25% EtOAc/Hexanes, n-phase silica; develop iodine; approx. Rf iodide 0.65, hydroxy 0.25). After purging the reaction flask well with an inert gas, the catalyst was removed by filtration through a bed of celite. When filtering out the catalyst, care was taken to keep the catalyst wet. Also, due to the large loading of catalyst, an alternative method of filtration, with the elimination of celite was sometimes used to allow for recycling the catalyst. The filter cake was rinsed several times with tetrahydrofuran or methylene chloride. The reaction mixture was then concentrated to near dryness, taken up in methylene chloride, rinsed with distilled water (2x), and dried over anhydrous sodium sulfate. After removal of the drying agent, the solvent was removed on a rotoevaporater. The pinkish product was purified by recrystallization from ethanol. The material was then bleached with decolorizing carbon to remove colored impurities.

We claim:

1. A method for making 3α-hydroxy,3β-substituted-pregnanes
   wherein the 3β group is selected from
   1) —$CH_2$—Y—R1 wherein R1 is selected from a halogenated or unhalogenated $C_1$ radical, a $C_2$-$C_6$ saturated or unsaturated, halogenated or unhalogenated straight chain radical, a $C_3$-$C_6$ saturated or unsaturated, halogenated or unhalogenated branched chain radical, a $C_3$-$C_6$ cyclic radical, or $C_5$-$C_6$ aromatic radical, and a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
   2) —$CH_2$—Y—$CH_2$—R1' wherein R1' is selected from R1 and hydrogen; and
   3) an R2 group wherein R2 is selected from a halogenated or unhalogenated $C_1$ radical, a $C_2$-$C_4$ saturated or unsturated, halogenated or unhalogenated straight chain radical, and a $C_3$-$C_4$ saturated or unsturated, halogenated or unhalogenated branched chain radical; and

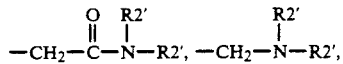

—$CH_2$—C≡N, —$CH_2$—SCN, —$CH_2$—N=N=N and —C≡N wherein R2' is selected from R2 and hydrogen; by forming a 3(R)-pregnan-3-spiro-2'oxirane-20-one through chemoselective and diastereoselective reaction at the 3-keto position of a pregnan-3,20-dione, and opening said 3(R)-pregnan-3-spiro-2'oxirane-20-one in a regioselective fashion, without protecting the 20-keto position.

2. A method for making a 3α-hydroxy,3β-methyl-pregnane-20-one wherein the steps comprise:
   A) reacting trimethyl sulfoxonium iodide with NaH in DMSO or with potassium t-butoxide in THF to form an ylide;
   B) reacting said ylide with a pregnan-3,20-dione to form a 3(R)-pregnan-3-spiro-2'oxirane-20-one; and
   C) reacting said 3(R)-pregnan-3-spiro-2'oxirane-20-one with sodium iodide and tributyl tin hydride in 1,2-dimethoxyethane.

3. A method for making a 3α-hydroxy,3β-methyl-pregnane-20-one wherein the steps comprise:
   A) reacting trimethyl sulfoxonium iodide with NaH in DMSO or with potassium t-butoxide in THF to form an ylide;
   B) reacting said ylide with a pregnan-3,20-dione to form a 3(R)-pregnan-3-spiro-2'oxirane-20-one; and
   C) reacting said 3(R)-pregnan-3-spiro-2'oxirane-20-one with sodium iodide, hydrogen gas and palladium on carbon in a mixture of THF and methanol.

4. A method for making a 3α-hydroxy,3β-substituted-pregnane-20-one
   wherein the 3β group is selected from
   1) —$CH_2$—Y—R1 wherein R1 is selected from a halogenated or unhalogenated $C_1$ radical, a $C_2$-$C_6$ saturated or unsaturated, halogenated or unhalogenated straight chain radical, a $C_3$-$C_6$ saturated or unsaturated, halogenated or unhalogenated branched chain radical, a $C_3$-$C_6$ cyclic radical, or $C_5$-$C_6$ aromatic radical, and a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
   2) —$CH_2$—Y—$CH_2$—R1' wherein R1' is selected from R1 and hydrogen; and
   3) an R2 group wherein R2 is selected from a halogenated or unhalogenated $C_1$ radical, a $C_2$-$C_4$ saturated or unsturated, halogenated or unhalogenated straight chain radical, and a $C_3$-$C_4$ saturated or unsturated, halogenated or unhalogenated branched chain radical; and

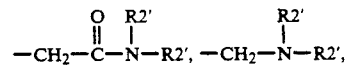

—$CH_2$—C≡N, —$CH_2$—SCN, —$CH_2$—N=N=N and —C≡N wherein R2' is selected from R2 and hydrogen;
   wherein the steps comprise:
   A) reacting trimethyl sulfoxonium iodide with a base that forms a conjugate acid which has $pK_a > 15$ in a a non-carbonyl polar aprotic solvent to form an ylide;
   B) reacting said ylide with a pregnan-3,20-dione to form a 3(R)-pregnan-3-spiro-2'oxirane-20-one; and
   C) reacting said 3(R)-pregnan-3-spiro-2'oxirane-20-one in a suitable solvent that can dissolve, but does not react with, the oxirane or the nucleophile with a nucleophile capable of reacting at the 3' position of said oxirane to open said oxirane ring.

5. The method of claim 4 wherein the suitable base of step (A) is selected from the group consisting of NaH, potassium t-butoxide, and $NaNH_2$.

6. The method of claim 4 wherein the nucleophile of step (C) is selected from the group consisting of alkoxides, thioalkoxides, azides, cyanides, isocyanides, amines, and halide anions.

7. The method of claim 6 wherein the 3α-hydroxy,3β-substituted-pregnane-20-one contains a 3β-ethyl group and the nucleophile of step (C) is dimethyl lithium cuprate.

8. The method of claim 6 wherein the 3α-hydroxy,3β-substituted-pregnane-20-one contains a 3β-bromomethyl group and the nucleophile of step (C) is sodium bromide.

9. The method of claim 6 wherein the 3α-hydroxy,3β-substituted-pregnane-20-one contains a 3β-azidomethyl group and the nucleophile of step (C) is sodium azide or trimethylsilyl azide.

10. The method of claim 6 wherein the 3α-hydroxy,3β-substituted-pregnane-20-one contains a 3β-propyl group and the nucleophile of step (C) is diethyl lithium cuprate.

11. The method of claim 6 wherein the 3α-hydroxy,3β-substituted-pregnane-20-one contains a 3β-trifluoroethyloxymethyl group and the nucleophile of step (C) is sodium trifluoroethoxide.

12. The method of claim 6 wherein the 3α-hydroxy,3β-substituted-pregnane-20-one contains a 3β-iodomethyl group and the nucleophile of step (C) is sodium iodide.

13. The method of claim 12 wherein the 3β-iodomethyl group is further reacted with sodium benzyloxide to form a 3β-benzyloxy group.

14. The method of claim 13 wherein the 3β-benzyloxy group is hydrogenolyzed to form a 3β-hydroxymethyl group.

15. The method of claim 12 wherein the 3β-iodomethyl group is further reacted with sodium methoxide to form a 3β-methoxymethyl group.

16. The method of claim 4 wherein the 20-keto group of the 3α-hydroxy,3β-substituted-pregnane-20-one is further reduced, condensed, oxidized, substituted or eliminated after formation of said oxirane ring.

* * * * *

UNITED STATES PATENT AND TRADEMARK OFFICE
CERTIFICATE OF CORRECTION

PATENT NO. : 5,319,115
DATED : June 7, 1994
INVENTOR(S) : Tahir, et al

It is certified that error appears in the above-indentified patent and that said Letters Patent is hereby corrected as shown below:

On the title page, item [73] Assignee:"Cocensys Inc., Irvine, Calif" should read --CoCensys Inc., Irvine Calif.; University of Southern California, Los Angeles, Calif.

Signed and Sealed this

Twenty-first Day of February, 1995

Attest:

Attesting Officer

BRUCE LEHMAN

Commissioner of Patents and Trademarks